United States Patent [19]

Koch et al.

[11] 4,380,647

[45] Apr. 19, 1983

[54] 2-AMINOPYRROLIN 5-ONES AND AMINOCYCLOPROPYL ISOCYANATES THEREFROM

[75] Inventors: Tad H. Koch; Barry J. Swanson, both of Boulder, Colo.

[73] Assignee: University Patents, Inc., Norwalk, Conn.

[21] Appl. No.: 240,043

[22] Filed: Mar. 3, 1981

[51] Int. Cl.$^3$ ............... C07D 207/26; C07C 118/00; C07C 119/045
[52] U.S. Cl. ........................... 548/519; 204/158 R; 204/159.11; 260/453 A; 260/453 AR; 260/453 P; 528/45; 528/423
[58] Field of Search ................ 260/326.5 J, 453 A, 260/326.2, 453 AR, 453 P; 204/158 R; 548/519

[56] References Cited

PUBLICATIONS

Comstock et al., Am. Chem. J., (1891), 13, 522.
Nagasaka et al., Heterocycles, vol. 9, No. 10, pp. 1375-1380 (1978).
Koch et al., J. Am. Chem. Soc., 95, 2957 (1973).

Primary Examiner—Dolph H. Torrence
Attorney, Agent, or Firm—Philip Hill

[57] ABSTRACT

Subjecting 1,4-bis-[(pyrrolin-3-onyl)methylamino]-2-butyne to ultraviolet irradiation effects rearrangement in greater than 80% yield to 1,4-bis-[(isocyanatocycloprolpyl)methylamino]-2-butyne. The diisocyanate is useful in the synthesis of polyurethanes and polyureas and also for the in situ photochemical generation of a cross-linking agent for polyurethanes and structurally related polymers.

14 Claims, 2 Drawing Figures

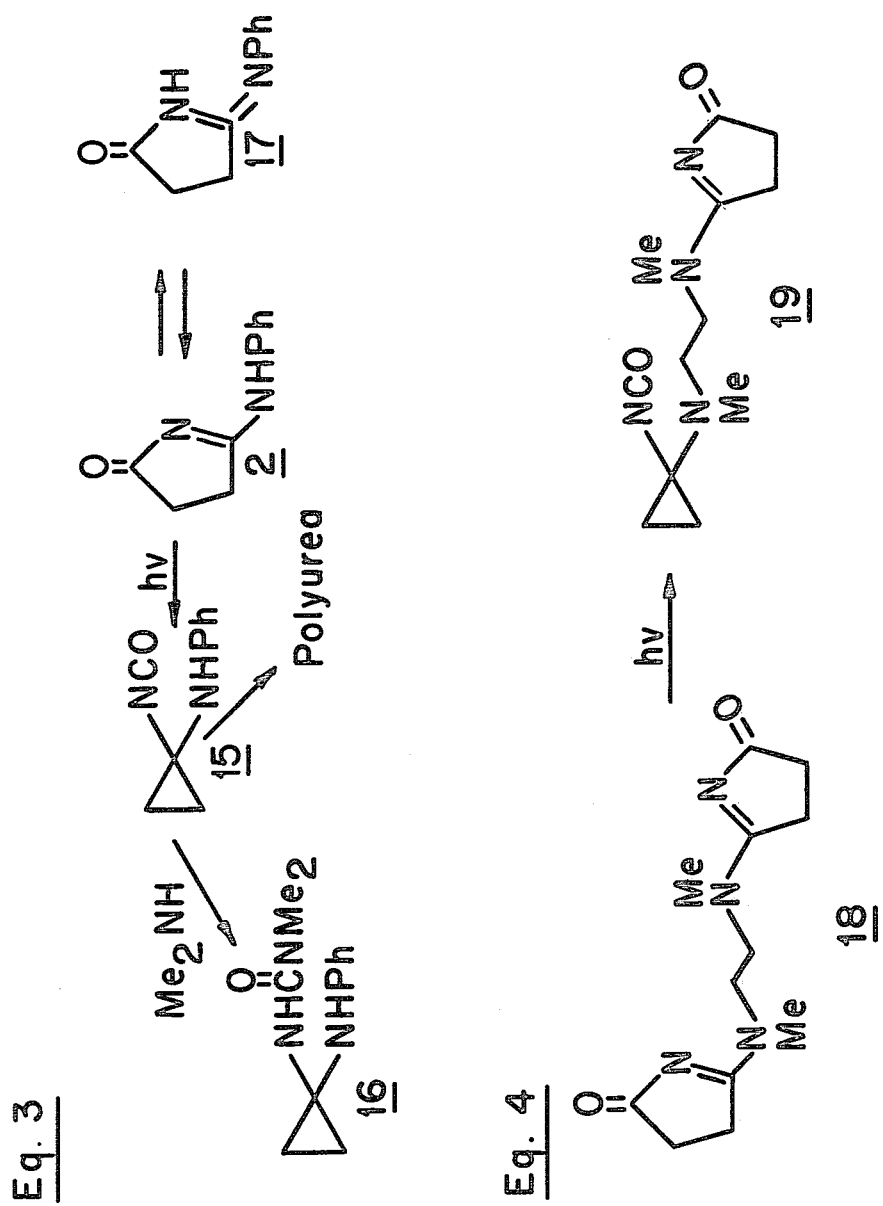

2-AMINOPYRROLIN 5-ONES AND AMINOCYCLOPROPYL ISOCYANATES THEREFROM

This invention was made in the course of research work supported by grants from the National Institute of General Medical Sciences.

This invention relates to novel 2-aminopyrrolin-5-one compositions and to the novel aminocyclopropyl isocyanates produced therefrom by photochemical rearrangement. More particularly, this invention relates to bis-(2-aminopyrrolin-5-ones) and to the bis-(aminocyclopropyl isocyanates) produced therefrom by photochemical rearrangement. In a specific aspect, this invention relates to the photochemical rearrangement of 1,4-bis[(pyrrolin-3-onyl)methylamino]-2-butyne to 1,4-bis-[isocyanatocyclopropyl)-methylamino]-2-butyne; and 1,4-bis[(pyrrolin-3-onyl)phenylamino]-2-butyne to 1,4-bis[(isocyanatocyclopropyl)phenylamino]-2-butyne.

This invention further relates to the production of novel polymers, such as polyurethanes, polyureas, and mixtures thereof, by the reaction of the aforementioned isocyanates with suitable alcohols and amines.

This invention still further relates to the in situ photochemical generation of a cross-linking agent for polyurethanes, polyureas, and structurally related polymers.

The synthesis of 2-ethoxypyrrolin-5-ones and their reaction with aniline to give 2-anilinopyrrolin-5-ones have been reported by Comstock et.al.; Am. Chem. J. 1891, 13,522; and Nagasaka et.al., Heterocycles, 1978, 9, 1375. The photochemical rearrangement of 2-ethoxypyrrolin-5-ones to ethoxy cyclopropyl isocyanates has been reported by Koch et.al., J. Am. Chem. Soc. 1973, 95,2957.

The principal disability of the above-described compounds is their instability to water and other moderate nucleophiles. For example, exposure to atmospheric moisture at ambient temperatures results in rapid hydrolysis of the alkoxy group. Thus, use of alkoxy derivatives is precluded in application where moisture stability is a requirement.

Accordingly, it is an object of this invention to provide pyrrolin-5-ones that rearrange to cyclopropyl isocyanates in high yields upon ultraviolet irradiation.

It is a further object of this invention to provide stable bis-ketoamidines that rearrange to cyclopropyl diisocyanates in high yields upon ultraviolet irradiation.

It is a further object of this invention to provide novel polymers derived from the reaction of such diisocyanates with suitable alcohols, amines, or mixtures thereof.

Similarly, it is a further object of this invention to provide for the in situ photochemical generation of a cross-linking agent for polyurethanes, polyureas, and structurally related polymers.

These and other objects will become apparent as description of the invention proceeds.

FIGS. 1 and 2, accompanying this specification, set forth chemical equations which serve to illustrate, without limitation, certain aspects of this invention.

In accordance with this invention it has been found that 2-ethoxypyrrolin-5-one(1) reacts with bis-secondary amine by nucleophilic addition to yield 2-aminopyrrolin-5-one derivative, as shown in equation (1) of FIG. 1, where R and R' are hydrocarbyl substituents such as alkyl, aryl, alkaryl, and aralkyl groups containing from 1 to about 12 carbon atoms, and x is a rigid bridging unit, for example, ¼-substituted butyne-2, 1,4-substituted trans-butene-2, bis-methyl substituted m- or p-xylene and hydrocarbyl substituted derivatives thereof containing from 1 to about 12 carbon atoms. Butyne-2 is a preferred bridging unit because it is especially effective with respect to rigidity and its ability to minimize detrimental through-space interactions of the chromophore groups during subsequent photorearrangement reactions. The nucleophilic addition can be carried out by addition of the secondary amine to 1 in an anhydrous, inert solvent at temperatures ranging from about ambient temperature to about the boiling point of the solvent employed. Suitable solvents include aliphatic and aromatic hydrocarbons, ethers, ketones, tetrahydrofuran, and the like. In specific nucleophilic additions, 1,4-bis(-methylamino)-2-butyne reacted with 2 equivalents of 1 at ambient temperature 1 hr. in 1:1 acetone-ether mixture to yield the bis-adduct in 93% yield. 1,4-Dianilino-2-butyne was less reactive and the addition of 2 equivalents of 1 was accomplished stepwise. The mono-adduct was prepared by reaction in neat mixture at ambient temperature, and the bis-adduct was subsequently prepared in refluxing toluene in 68% yield.

The photochemical rearrangement of the 2-aminopyrrolin-5-ones to the corresponding cyclopropyl isocyanates was effected according to the scheme set forth in equation (2a) of FIG. 1. The bichromophoric systems, 6 and 8, were irradiated in acetonitrile solvent at 2537 Å in a Rayonet Reactor. Reactions were monitored by IR spectroscopy and thin layer chromatography. The IR spectra indicated formation of the isocyanate functional group, characterized by an intense stretching band in the region of 4.4 to 4.5 $\mu$m. The isocyanates were not isolated but were trapped as dimethylurea derivatives by the addition of dimethylamine to the photolysates (equation (2b) of FIG. 1). The dimethylureas proved to be nicely crystalline, easily characterized derivatives. Product 13 was obtained in 85% yield, and product 14 in 92% yield.

The photorearrangement of 2-aminopyrrolin-5-ones prepared by the addition of primary amines to 2-ethoxypyrrolin-5-one was also examined. 2-Anilino-pyrrolin-5-one was prepared as described by Comstock et.al. Although it underwent photorearrangement to anilinocyclopropyl isocyanate (15), shown in equation (3) of FIG. 2, the isolated yield of the dimethylurea derivative 16 was poor (<10%). Possible explanations for the low yield are the presence of the light absorbing tautomer 17 and the polymerization of 15. Evidence for the tautomerism is the observed shift in the UV band maximum to 265 nm.

The butyne linkage in the bichromophoric systems 6 and 8 was selected to minimize through-space interaction of the chromophores during the photorearrangement. Through-space interaction is inhibited by the rigidity of the alkyne functional group. The need to minimize through-space interaction was evident from a preliminary investigation of the photorearrangement of 1,2-bis[2-(pyrrolin-5-onyl)methylamino ethane] (18), as shown in equation (4) of FIG. 2. The bichromophoric system 18 rearranged in poor yield only to the mono-aminocyclopropyl isocyanate 19. On the basis of this result and the successful rearrangement of 6 and 8 to bis-aminocyclopropyl isocyanates 11 and 12, it appears that through-space interactions in excited 19 and possibly also in excited 18 inhibit the photochemical rearrangement. The through-space interaction in excited 19 probably involves electron transfer from the amino substituent to the excited keto amidine functional group with the possible intermediacy of an intramolecular exciplex. Intramolecular electron transfer could result in quenching of excited 19 and/or the formation of reactive radicals.

The aminopyrrolin-5-ones and the corresponding isocyanates produced in accordance with this invention are useful intermediates for the synthesis of natural products and pharmaceutical compositions. The isocyanates can also serve as monomers in the production of polyurethanes and polyureas. The biochromophoric systems 1,4-bis[(pyrrolin-3-onyl)methylamino]-2-butyne (6) and 1,4-bis[(pyrrolin-3-onyl)phenylamino]-2-butyne (8) can be employed to advantage for the photochemical generation of the corresponding bis-isocyanates in situ as cross-linking agents for polyurethanes and polyureas. The bis-aminopyrrolines 6 and 8 are stable to water and alcohols, intensely absorb ultraviolet light, and efficiently rearrange to bis-isocyanates.

For example, in the preparation of polyurethanes reaction may be effected with any suitable diol or polyol. These include glycols such as ethylene glycol and 1,4-butandiol, and diols such as 1,4-bis-hydroxymethyl benzene. In the preparation of polyureas, suitable polyamino include hexamethylene diamine, ethylene diamine, p-phenylene diamine, and the like. Where desired mixtures of polyols and polyamines may be employed.

When the novel disocyanates of this invention are employed as cross-linking agents, only a minor proportion, for example, from about 2 to about 10, mole %, is required in admixture with suitable monomeric or prepolymeric mixtures. The reactive diisocyanate is prepared in situ by UV irradiation of the corresponding amino-pyrrolinone.

Such in situ preparation of the diisocyanates of this invention may be employed generally, if desired, in the preparation of polymers in accordance with this invention.

In situ preparation of a corresponding monoisocyanate permits the termination of chain growth in any otherwise conventional formation of a polyurethane, polyurea, or structurally similar polymer.

DESCRIPTION OF THE PREFERRED EMBODIMENTS

Figure 1:
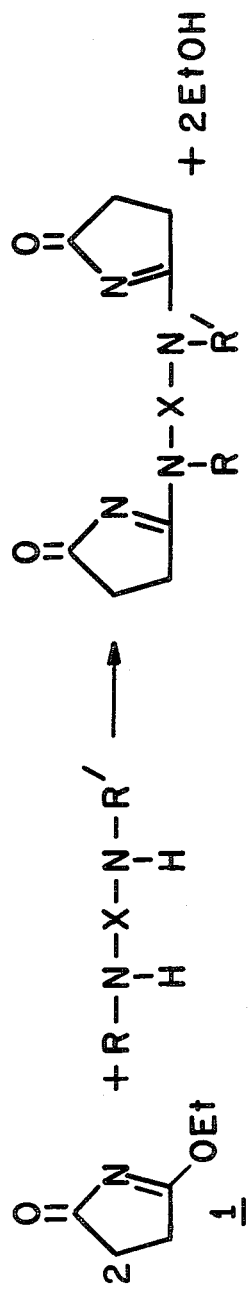
Figure 1:
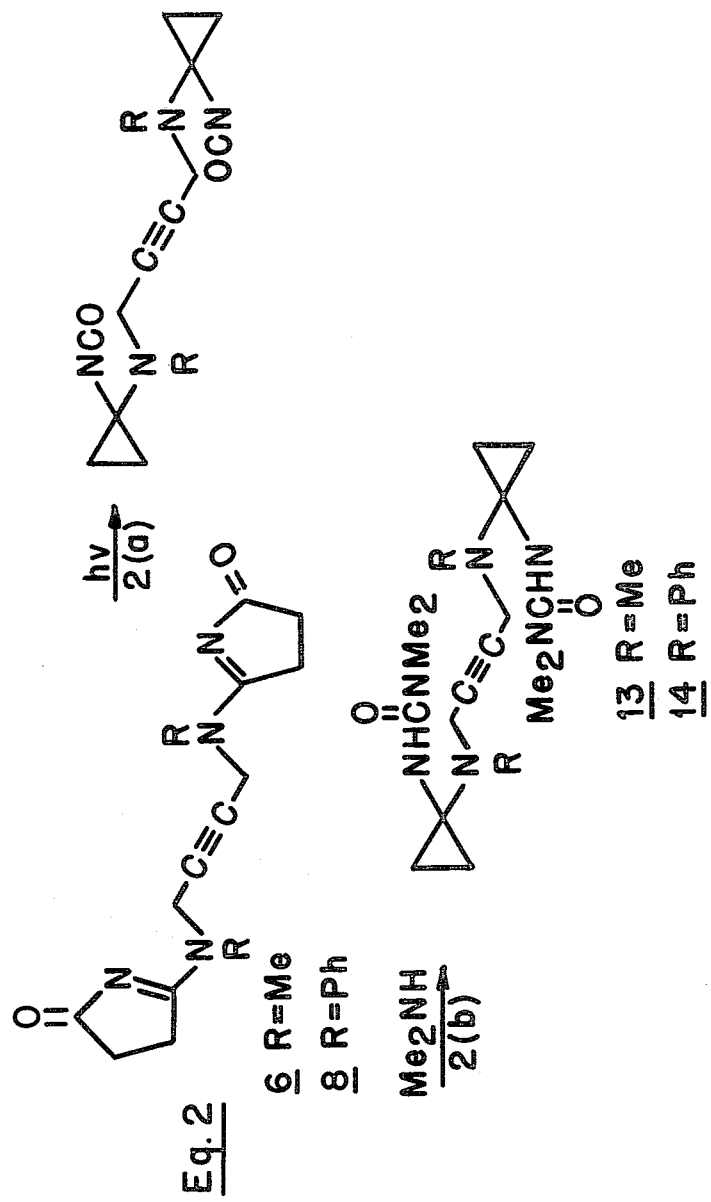

The invention is further illustrated, without limitation, by reference to the following examples and procedures.

Melting points were measured with Fisher-Johns and Hoover-Thomas melting point apparati and are uncorrected. Perkin-Elmer 337 and Varian 635 spectrophotometers were used to determine IR and UV spectra, respectively. $^1$H-NMR spectra were recorded with a Varian EM-390 spectrometer, and chemical shifts are reported in δ units from internal tetramethylsilane. Mass spectra were measured at 70 eV with Varian MAT CH-5 and CH-7 spectrometers. Microanalyses were performed by Atlantic Microlab, Atlanta, Ga., and exact molecular weights were obtained at the Regional Mass Spectrometry Lab at The University of Nebraska, Lincoln, Nebr. 2-Ethoxypyrrolin-5-one was prepared from succinimide as previously described. 1,4-bis(methylamino)-2-butyne and 1,4-dianilino-2-butyne were prepared from 1,4-dichloro-2-butyne. Tetrahydrofuran was distilled from lithium aluminum hydride prior to use.

EXAMPLE 1

1,4-bis[(pyrrolin-3-onyl)methylamino]-2-butyne (6)

To a stirred solution of 2.28 g (18.0 mmol) of 2-ethoxypyrrolin-5-one in 20 ml of 1:1 (v/v) mixture of acetone and anhydrous ether was added 1.02 g (9.1 mmol) of 1,4-bis(methylamino)-2-butyne dropwise. After 2 hours a white precipitate formed which was collected by vacuum filtration to give 2.3 g (93%) of 6. The material obtained was pure by $^1$H-NMR spectroscopy and gave a mp 189°–191° C. with decomposition. An analytical sample, prepared by recrystallization from a chloroform-acetone solution (1:5 v/v), had the following physical and analytical properties: mp 191°–192° C. decomposition; IR (CH$_2$Cl$_2$) 5.81 and 6.38 μm; $^1$H-NMR (D$_2$O) δ2.2–3.1 (m, 4H), 3.08 (s, 3H), and 4.14, 4.15, 4.22 ppm (three singlets, total integration 3H); UV (MeOH) 235 nm (ε57,600); mass spectrum m/e (rel.intensity) 274 (43), 163 (19) 161 (base), 160 (13), 135 (29), 134(83), 133 (54), 121 (12), 113 (15), 112 (66), 111 (12), 82 (14), 80 (57), 79 (12), 69 (15), 68 (37), 66 (10), 58 (36), 56 (31), 55 (25), 54 (25), 43 (19), 42 (44), 41 (16).

Anal. Calcd. for C$_{14}$H$_{18}$N$_4$O$_2$: C, 61.30; H, 6.61; N, 20.42. Found: C, 61.09; H, 6.65; N, 20.32.

EXAMPLE 2

1,4-bis[(pyrrolin-3-onyl)phenylamino]-2-butyne (8)

An intimate mixture of 450 mg (1.91 mol) of 1,4-dianilino-2-butyne and 24.3 mg (1.9 mol) of 2-ethoxypyrrolin-5-one was stored at ambient temperature for 2 days. The resultant solid was suspended in anhydrous ether and collected by vacuum filtration. The solid was identified spectrophotometrically as the mono-adduct. The mono-adduct and 1.00 g (7.87 mol) of 2-ethoxypyrrolin-5-one in toluene solvent (41 ml) were then refluxed under a nitrogen atmosphere for 1 day. After cooling, 382 mg of 8 as a slightly brown solid was collected by vacuum filtration. The mother liquor was concentrated and allowed to stand for 5 days. An additional 152 mg of product was collected by vacuum filtration (combined yield of (8) 68%). To prepare an analytical sample, the material was dissolved in chloroform and decolorized with charcoal. After rotary evaporation of the chloroform, the resulting colorless solid was collected by vacuum filtration and washed with anhydrous ether. This material had the following physical properties: mp 214.5–215.5; IR (CHCl$_3$) 5.82 and 6.48 μm; $^1$H-NMR (CDCl$_3$) δ2.25–2.69 (m, 4H), 4.80 (s, 2H), and 7.22–7.63 ppm (m, 5H); UV (MeOH) 238 nm (ε53,000); mass spectrum m/e rel. intensity) 398 (1.2) 225 (37), 224 (82), 197 (17), 196 (base), 195 (88), 174 (19), 147 (14), 146 (22), 142 (24), 131 (14), 130 (28), 119 (75), 118 (24), 115 (15), 104 (27), 92 (19), 90 (22), 76 (95), 75 (12), 54 (14), 53 (12), 51 (40), 39 (15), and 28 (22).

Anal. Calcd. for C$_{24}$H$_{22}$N$_4$O$_2$: C, 72.34; H, 5.56; N, 14.06. Found: C, 72.55; H, 5.68; N, 13.91.

The structural assignments for the keto amidines are completely consistent with the spectral and analytical data obtained. The $^1$H-NMR spectrum of the bis-adduct 8 suggests that this compound exists as a single conformer or that the barrier to rotation about the carbon-nitrogen single bond is significantly lower than the barrier in the bis-adduct 6.

Ultraviolet Absorption. The ketoamidine functionality gives rise to intense ultraviolet absorption with maxima in the region of 235 to 239 nm in tetrahydrofuran and methanol solvents. The magnitude of the molar extinction coefficients, which range from 26,000 to 58,000, and the lack of solvent shift indicate a π-π* transition. There is no resolved n-π* band. The UV spectral properties are in contract with those of the 2-ethoxypyrrolin-5-ones which show distinct n-π* bands in the region of 275 nm and only end absorption for the π-π* transitions. It has been discovered that substitution of an amino substituent for an ethoxy substituent results in a significant red shift of the π-π* transition with probably little shift in the n-π* transition. No through-bond or through-space coupling of the two ketoamidine functional groups in the ground state of the bichromophoric systems (6 and 8) is apparent from the UV spectra.

EXAMPLE 3

1,4-bis[N,N'-(dimethylamido)aminocyclopropyl)-N-methylamino]-2-butyne (13)

A 10 ml quartz test tube was charged with 44 mg (0.161 mmol) of 1,4-bis[(pyrrolin-3-onyl)methylamino]-2-butyne (6) and 10 ml of reagent grade acetonitrile. The test tube was equipped with a nitrogen inlet and outlet and a cold finger. The solution was degassed for 10 minutes prior to, and during, the irradiation in a Rayonet Reactor equipped with 2537 A° lamps. After 2.5 hours of irradiation the starting material had disappeared as determined by IR spectroscopy. Dimethylamine was then bubbled through the photolysis mixture for 10 minutes. Rotary evaporation of the solvent yielded 50 mg (85%) of 13 as a yellow solid which was pure as indicated by $^1$H-NMR spectroscopy. The material had the following physical properties: mp 166°-167° C. dec.; IR (CH$_2$Cl$_2$) 2.91, 3.41, 6.03, and 6.66 μm; $^1$H-NMR (CDCl$_3$) δ0.91 (s, 8H), 2.41 (s, 6H), 2.79 (s, 12H), 3.48 (s, 4H), and 5.06 (broad, 2H); mass spectrum m/e (rel.intensity) 208 (15), 207 (12), 162 (17), 156 (12), 87 (15), 72 (base), 68 (11), 44 (45), 43 (15), 42 (15). The material could not be sufficiently purified for elemental analysis. The highest m/e peak in the high resolution mass spectrum corresponded to M+—N(CH$_3$)$_2$: calcd. for C$_{16}$H$_{26}$N$_5$O$_2$: 320.2077; found: 320.2082.

EXAMPLE 4

1,4-bis[N-(N'(dimethylamido)aminocyclopropyl)-N-phenylamino]-2-butyne (14)

A 10 ml quartz test tube was charged with 49.8 mg (0.125 mmol) of 1,4-bis[(pyrrolin-3-onyl)phenylamino]-2-butyne (8) in 10 ml of reagent grade acetonitrile. The test tube was equipped with cold finger and nitrogen inlet and outlet. The solution was degassed for 10 minutes prior to and during irradiation in a Rayonet Reactor equipped with 2537 Å lamps. After 1.0 hour of irradiation the starting material had disappeared as indicated by IR spectroscopy. Dimethylamine was then bubbled through the solution for 10 minutes. Rotary evaporation of the solvent yielded 56.1 mg of 14 (92%) as a slightly yellow solid mp 180°-181° C. dec. which was pure by $^1$H-NMR spectroscopy. An analytical sample of 14 prepared by alumina TLC eluting with ethyl acetate had the following physical properties: mp. 179°-181° C. dec; IR (CH$_2$Cl$_2$) 2.91, 3.40, 6.05, and 6.66 μm; $^1$H-NMR (CDCl$_3$) δ1.20 (s, 8H), 2.77 (s, 12H), 4.42 (s, 4H), 5.48 (broad, 1H), and 6.66-7.40 ppm (m, 10H); mass spectrum m/e (rel.intensity) 488 (3.5), 372 (13), 270 (25), 269 (13), 225 (30), 220 (20), 218 (12), 198 (12), 197 (20), 183 (14), 143 (11), 132 (14), 130 (16), 72 (base). The material could not be sufficiently purified for elemental analysis. The highest m/e peak in the high resolution mass spectrum corresponded to the molecular ion: calcd. for C$_{28}$H$_{36}$N$_6$O$_2$, 488.2900; found: 488.2893.

EXAMPLE 5

Polyurethane

A quartz tube is charged with 1,4-bis[(pyrrolin-3-onyl)methylamino]-2-butyne and acetonitrile as in Example 3, together with an equimolar quantity of 1,4-butylene glycol. Degassing and irradiation are conducted as before. Rotary evaporation of the solvent provides a tough, polymeric residue of the corresponding polyurethane.

EXAMPLE 6

Polyurea

The procedure of Example 5 is repeated except for the use of an equimolar quantity of p-phenylene diamine. There is provided a tough, polymeric residue of the corresponding polyurea.

Although this invention has been described in particular reference to certain embodiments thereof, it is understood that variations and modifications can be effected within the spirit and scope of the appended claims. It is intended that all the material contained in the above description and examples shall be interpreted in an illustrative and not in a limiting sense.

What is claimed is:

1. Bis-(2-aminopyrrolin-5-ones) characterized by the structure

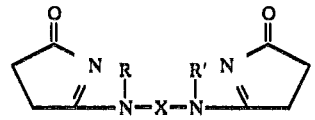

where R and R' are hydrocarbyl substituents containing from 1 to about 12 carbon atoms and are selected from the class consisting of alkyl, aryl, alkaryl, and aralkyl groups, and X is a substantially rigid bridging unit selected from the group consisting of 1,4-substituted butyne-2, 1,4-substituted trans-butene-2, bis-methyl substituted m-xylene, bis-methyl substituted p-xylene, and said hydrocarbyl substituted derivatives thereof.

2. The bis-(2-aminopyrrolin-5-one) of claim 1 wherein X is 1,4-substituted butyne-2 and both R and R' are methyl groups.

3. The bis-(2-aminopyrrolin-5-one) of claim 1 wherein X is 1,4-substituted butyne-2 and both R and R' are phenyl groups.

4. A process for the preparation of bis-(2-aminopyrrolin-5-ones) comprising the nucleophilic addition of a bis-secondary diamine to 2-ethoxypyrroline-5-one in an anhydrous, inert solvent at temperatures ranging from about ambient temperature to about the boiling point of the solvent employed, said secondary amine having the formula RNH-X-NHR' where R and R' are hydrocarbyl substituents containing from 1 to about 12 carbon atoms and are selected from the class consisting of alkyl, aryl, alkaryl, and aralky groups, and X is a substantially rigid bridging unit selected from the group consisting of 1,4-substituted butyne-2, 1,4-substituted trans-butene-2, bis-methyl substituted m-xylene, and said hydrocarbyl substituted derivatives thereof.

5. The process of claim 4 wherein the secondary diamine is 1,4-bis(methylamino)-2-butyne, the solvent is an acetonediethyl ether mixture, and the reaction is carried out at ambient temperature.

6. The process of claim 4 wherein the secondary diamine is 1,4-dianilino-2-butyne, the reaction is carried out neat at ambient temperature to give an intermediate reaction product, which intermediate product is treated with an additional amount of 2-ethoxypyrrolin-5-one in toluene solution at the reflux temperature of toluene to yield said bis-(2-aminopyrrolin-5-one).

7. Bis-(aminocyclopropyl isocyanates) characterized by the structure

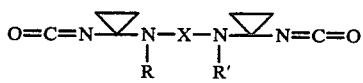

where R and R' are hydrocarbyl substituents containing from 1 to about 12 carbon atoms and are selected from the class consisting of alkyl, aryl, alkaryl, and aralkyl groups, and X is a substantially rigid bridging unit selected from the group consisting of 1,4-substituted butyne-2, 1,4-substituted trans-butene-2, bis-methyl substituted m-xylene, bis-methyl substituted p-xylene, and said hydrocarbyl substituted derivatives thereof.

8. The bis-(aminocyclopropyl isocyanate) of claim 7 wherein X is 1,4-substituted butyne-2 and both R and R' are methyl groups.

9. The bis-(aminocyclopropyl isocyanate) of claim 7 wherein X is 1,4-substituted butyne-2 and both R and R' are phenyl groups.

10. A process for the preparation of bis-(aminocyclopropyl isocyanates) comprising the photochemical rearrangement of bis-(2-aminopyrroline-5-ones) having the structure

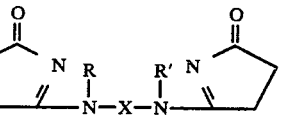

where R and R' are hydrocarbyl substituents containing from 1 to about 12 carbon atoms and are selected from the class consisting of alkyl, aryl, alkaryl, and aralkyl groups, and X is a substantially rigid bridging unit selected from the group consisting of 1,4-substituted butyne-2, 1,4-substituted trans-butene-2, bis-methyl substituted m-xylene, bis-methyl substituted p-xylene, and said hydrocarbyl substituted derivatives thereof.

11. The process of claim 10 wherein both R and R' are methyl groups and wherein the photochemical rearrangement of the bis-(aminopyrrolin-5-one) is effected in acetonitrile solution by irradiation with ultraviolet light.

12. The process of claim 10 wherein both R and R' are phenyl groups and wherein the photochemical rearrangement of the bis-(aminopyrrolin-5-one) is effected in acetonitrile solution by irradiation with ultraviolet light.

13. The process of claim 11 wherein both R and R' are methyl groups and wherein the irradiation is effected in acetonitrile solution with an ultraviolet source providing irradiation principally of about 2537 Angstrom units.

14. The process of claim 12 wherein both R and R' are phenyl groups and wherein the irradiation is effected in acedonitrile solution with an ultraviolet source providing irradiation principally of about 2537 Angstrom units.

* * * * *